US006472417B1

(12) United States Patent
Kodama et al.

(10) Patent No.: US 6,472,417 B1
(45) Date of Patent: Oct. 29, 2002

(54) SYNERGISTIC PESTICIDAL COMPOSITION OF PYRETHROID AND N-PHENYL-PYRAZOLE

(75) Inventors: Hiroshi Kodama, Wakayama (JP); Yasuhiro Wada, Osaka (JP); Rikio Yamaguchi, Osaka (JP)

(73) Assignee: Rhone-Poulenc Agrochimie, Lyon Cedex (FR)

( * ) Notice: Subject to any disclaimer, the term of this patent is extended or adjusted under 35 U.S.C. 154(b) by 0 days.

(21) Appl. No.: 10/175,111

(22) Filed: Jun. 20, 2002

Related U.S. Application Data

(62) Division of application No. 09/826,817, filed on Apr. 6, 2001, now Pat. No. 6,432,998, which is a division of application No. 09/457,861, filed on Dec. 10, 1999, now Pat. No. 6,258,835, which is a division of application No. 09/268,686, filed on Mar. 16, 1999, now Pat. No. 6,060,497, which is a division of application No. 08/855,606, filed on May 13, 1997, now Pat. No. 5,916,909, which is a division of application No. 08/700,520, filed as application No. PCT/EP95/00601 on Feb. 20, 1995, now Pat. No. 5,747,519.

(30) Foreign Application Priority Data

Feb. 27, 1994 (JP) .................................................. 6/52798

(51) Int. Cl.⁷ ........................ A01N 43/56; A01N 55/00; A01N 32/34
(52) U.S. Cl. .......................... 514/404; 514/63; 514/521
(58) Field of Search ................................ 514/404, 521, 514/63

(56) References Cited

U.S. PATENT DOCUMENTS

| 5,232,940 A | 8/1993 | Hatton et al. ................ 514/407 |
| 5,270,043 A | 12/1993 | Twinn et al. ................ 424/405 |
| 5,516,787 A | 5/1996 | Takada ........................ 514/407 |

FOREIGN PATENT DOCUMENTS

| EP | 0295117 | 12/1988 |
| EP | 0435609 | 7/1991 |
| FR | 2713891 | 6/1995 |
| WO | 93/06089 | 4/1993 |
| WO | 94/21606 | 9/1994 |

OTHER PUBLICATIONS

Colliot et al, Brighton Crop Protection Conference—Pests and Diseases—1992, 2–1, pp. 29–34 (Conference dates Nov. 23–25, 1992), published by The British Crop Protection Council, Farnham, Surrey, UK.

*The Pesticide Manual*, ninth edition, ed. Charles R. Worthing, 1991, pp. 662–663, published by The British Crop Protection Council, Farnham, Surrey, UK.

*Primary Examiner*—Allen J. Robinson
(74) *Attorney, Agent, or Firm*—Burns, Doane, Swecker & Mathis, L.L.P.

(57) ABSTRACT

The present invention provides an insecticidal composition comprising, as active ingredients, (a) at least one pyrethroid compound and (b) an N-arylpyrazole compound such as 5-amino-3-cyano-1-(2,6-dichloro-4-trifluoromethylphenyl)-4-trifluoromethylsulfmylpyrazole, and an insecticidal method which comprises applying the composition.

83 Claims, No Drawings

SYNERGISTIC PESTICIDAL COMPOSITION OF PYRETHROID AND N-PHENYL-PYRAZOLE

CROSS-REFERENCE TO RELATED APPLICATIONS

This application is a division of copending Application Ser. No. 09/826,817, filed Apr. 6, 2001, now allowed, which is a division of Application Ser. No. 09/457,861, filed Dec. 10, 1999, now U.S. Pat. No. 6,258,835, which is a division of Application Ser. No. 09/268,686, filed Mar. 16, 1999, now U.S. Pat. No. 6,060,497, which is a division of Application Ser. No. 08/855,606, filed May 13, 1997, now U.S. Pat. No. 5,916,909, which is a division of Application Ser. No. 08/700,520, filed Dec. 11, 1996, now U.S. Pat. No. 5,747,519, which is the U.S. national phase of International Patent Application Ser. No. PCT/EP95100601, filed Feb. 20, 1995 and designating the United States, which was published by the International Bureau in English as WO 95/22902 on Aug. 31, 1995. Applications Ser. Nos. 09/826,817, 09/457,861, 09/268,686 and 08/855,606 are incorporated by reference herein in their entireties and relied upon.

The present invention relates to a termite control composition for soil treatment containing a 3-cyano-1-(substituted phenyl)-pyrazole derivative and a pyrethroid compound as effective ingredients.

The pyrazole derivatives as effective ingredients of the termite control composition of the present invention are known compounds described in European patent publication 0295117 as well as in the international patent publications WO 93/06089 and 94/21606, which disclose that the compounds have a pesticidal effect on arthropods, vegetable nematodes, protozoan pests, and other pests. Many other pesticidal compounds can be used in combination with N-phenyl pyrazole derivatives. Pyrethroid compounds such as cyfluthrin, cypermethrin, deltamethrin, fenpropathrin, fenvalerate, and permethrin are recited among many possibilities without any reference to any specific effect in any conditions.

A first object of the instant invention is to provide synergistic compositions of 3-cyano-1-(substituted phenyl)-pyrazole derivatives.

Another object of the instant invention is to provide specific compositions which have an improved activity against pests, especially against insects.

Another object of the instant invention is to provide specific compositions which have an improved activity against termites.

There are mainly two types of termite control methods: namely, wood application by applying a control agent to wood, and soil treatment by spraying a control agent on the soil and/or under the floor. For existing houses, since the application of the agent to wood is rather difficult, soil treatment is generally used. In many cases, however, termites pass through the treated layer and eat the wood, and therefore, it is desired to develop a termite control agent which has both the termite control effect and the ability to prevent termites from passing through the pesticidally treated layer.

A further object of the instant invention is to provide a novel termite control composition (preferably for soil treatment) which has a strong termite control effect as well as the ability to prevent termites from passing through the pesticidally treated layer.

It has been found that these goals may be reached by means of the compositions of the instant invention.

The compositions of the present invention comprise, as effective ingredients, a pyrethroid compound and a compound of formula (I)

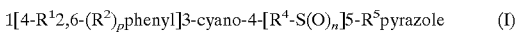

wherein:
  $R^1$ is halogen, lower haloalkyl, lower haloalkoxy or $SF_5$ (lower being an integer from 1 to 4, preferably one),
  $R^2$ is halogen, the various $R^2$ being identical or different,
  $R^1$ is halogen, lower alkyl or haloalkyl,
  $R^5$ is halogen, lower alkyl or amino,
  n is 0 or 1 or 2; p is 1 or 2 or 3 or 4, preferably 2.
  Halo before the name of a radical means that this radical may be substituted by one or more halogen atoms.

A preferred compound of formula (I) is 5-amino-3-cyano-1-(2,6-dichloro-4-trifluoromethylphenyl)-4-trifluoromethylsulphinylpyrazole (Compound A).

The compositions of the invention comprise a synergistic amount of active ingredients.

Pyrethroid compounds which can be used in the present invention include all kinds of pyrethroids, especially pyrethroids other than cyfluthrin, cypermethrin, deltamethrin, fenpropathrin, fenvalerate, and permethrin. Advantageously, pyrethroids which can be used in the invention are compounds selected from a group consisting of the following pyrethroid compounds, even though not limited to these pyrethroid compounds:

1. Allethrin [dl-3-allyl-2-methyl-4-oxo-2-cyclopentenyl-dl-cis, trans-chrysanthemate]
2. Ethofenprox [2-(4-ethoxyphenyl)-2-methylpropyl-3-phenoxybenzyl ether]
3. Cycloprothrin [(RS)-a-cyano-3-phenoxybenzyl (RS)-2,2-dichloro-1-(4-ethoxyphenyl)cyclopropane carboxylate]
4. Cyhalothrin [(RS)-a-cyano-3-phenoxybenzyl (Z)-(1RS, 3RS) 3-(2-chloro-3,3,3-trifluoro-1-propenyl)-2,2-dimethylcyclopropane carboxylate]
5. Cyfluthrin [(RS)-a-cyano-4-fluoro-3-phenoxybenzyl (1RS, 3RS)-(1RS, 3RS)-3-(2,2-dichlorovinyl)-2,2-dimethylcyclopropane carboxylate]
6. Cypermethrin [(RS)-a-cyano-3-phenoxybenzyl (1RS, 3RS)-(1RS,3SR)-3-(2,2-dichlorovinyl)-2,2-dimethylcyclopropane carboxylate]
7. Pyrethrin
8. Tralomethrin [(S)-a-cyano-3-phenoxybenzyl (1R,3S)-2,2-dinethyl-3-(1,2,2,2-tetrabromoethyl)cyclopropane carboxylate]
9. Fenvalerate [(RS)-a-cyano-3-phenoxybenzyl (RS)-2-(4-chlorophenyl)-3-methylbutanoate]
10. Fenpropathrin [(RS)-a-cyano-3-phenoxybenzyl-2,2,3,3-tetramethylcyclopropane carboxylate]
11. Flucythrinate [(RS)-a-cyano-3-phenoxybenzyl-(S)-2-(4-difluoromethoxyphenyl)-3-methyl butylate]
12. Permethrin [3-phenoxybenzyl (1RS,3RS)-(1RS,3RS)-(2,2-dichlorovinyl)-2,2-diimethylcyclopropane carboxylate]
13. Bifenthrin [2-methylbiphenyl-3-yl-methyl (Z)-1RS, 3RS)-3-(2-chloro-3,3,3-trifluoroprop-1-enyl)-2-2-dimnethylcyclopropane carboxylate]
14. Silafluofen [4-ethoxyphenyl-[3-(3-phenoxy-4-fluorophenyl)propyl](dimnethyl)silane]
15. Lesmethrin [5-benzyl-3-furylmethyl dl-cis, trans-chrysanthemate]
16. Tefluthrin [2,3,5,6-tetrafluoro-4-methylbenzyl-(1RS)-cis-3-(Z-2-chloro-3,3,3-trifluoroprop-1-enyl)-2,2-dimethylcyclopropane carboxylate]
17. Acrinathrin [(S)-a-cyano-3-phenoxybenzyl (Z)-(1R,3S)-2,2-dimnethyl-3-[2-(2,2,2-trifluoro-1-trifluoromethylethoxycarbonyl)vinyl]cyclopropane carboxylate]

18. Prarethrin [(RS)-2-methyl-4-oxo-3-prop-2-enylcyclopent-2-enyl (1RS)-cis,trans-2,2-dinethyl-3-(2-methylprop-i-enyl)cyclopropane carboxylate]
19. Cismethrin [5-benzyl-3-furylmethyl (1R)-trans-2,2-dimnethyl-3-(2-methylprop-1-enyl)cyclopropane carboxylate]
20. d-Phenothrin [3-phenoxybenzyl (1RS)-cis, trans-2,2-dimnethyl-3-(2-methylprop-1-enyl)cyclopropane carboxylate]
21. Deltamethrin [(S)-cyano-3-phenoxybenzyl (1R)cis-3-(2,2-dibromovinyl)-2,2-dimethylcyclopropane carboxylate]
22. Tetramethrin [cyclohex-1-ene-1,2-dicarboximide methyl (1RS,3RS, 1RS,3SR)-2,2-dimethyl-3-(2-methylprop-1-enyl)cyclopropane carboxylate].

The synergistic compositions of the invention are compositions wherein the ratio by weight of the pyrethroid compound to the compound of formula (I) is between 0.1 and 10, preferably between 0.5 and 5.

The synergistic compositions of the invention are compositions, which are most useful for termite control, preferably with soil treatment. Thus, the invention is also directed to a method of control of pests, especially of termites, which comprises applying an effective amount of the compositions according to the invention, as herein described.

The liquid compositions of the invention generally comprises 0.001 to 50% (all percentages are by weight in the instant specification, unless specifically indicated otherwise) of compound of formula (I), preferably from 0.005 to 10%. The concentrated compositions which are those used for storage and commercial purposes comprise generally from 1 to 20% of this compound of formula (I).

When the compositions for soil treatment of the present invention are used for termite control, especially for soil treatment and/or for treating under-floor soil, the quantity of the effective ingredient may be within a range between 0.01 g and 7 g, preferably between 0.1 g and 5 g per square meter. For wood treatment, such as timber or all kind of wood, the method of control of pests, especially of termites, according to the invention is impregnating the wood by means of a composition as hereinbefore defined.

The application of the compositions of the invention to animals is generally made at 0.1 to 100 mg, preferably at 2 to 20 mg per kilogram of body weight of the animal.

The termite control composition of the present invention has a high significant termite control effect on house damaging termites, for example *Coptotermes formosanusus* (Shiraki), *Reticulitermes speratus* (Kolbe), an *Odontotermes formosanusus* (Shiraki), and *Cryptotermes domesticus* (Haviland), as a well as the ability to prevent termites from passing through pesticidally treated materials. The composition may be applied to or adsorbed in building materials, furniture, leather, fabrics, vinyl coated articles, electric wires, or cables.

For the efficient use of the termite control composition for material or soil treatment of the present invention, the composition may be dissolved, suspended, mixed, adsorbed, or adhered on an appropriate solid-and/or liquid vehicle (this word is used as a synonym of "carrier") according to the formulation generally used, together with auxiliary agents if required. This composition may be formulated into forms suited to the object of use, for example, an oil solution, emulsion, water solution, powder, granules, wettable powder, aerosol, smoking agent, or flowable agent.

Solid vehicles used in the present invention include, for example, clays such as kaolin, bentonite, and acid clay; talc materials such as talc and pyrophylite; siliceous materials such as diatomaceous earth, silica sand, mica, synthetic silicates, and high dispersion synthetic silicates; and inorganic mineral powders such as pumice and sand. Liquid vehicles include, for example, alcohols such as methanol, ethanol, and ethylene glycol; ketones such as acetone, methyl ethyl ketone, and cyclohexanone; ethers such as ethyl ether, dioxane, tetrahydrofuran, and cellosolve; aliphatic hydrocarbons such as kerosene; aromatic hydrocarbons such as benzene, toluene, xylene, solvent naphtha, cyclohexane, and methyl naphthalene; and halogenated hydrocarbons such as chloroform, carbon tetrachloride, and chlorobenzene. These solid or liquid vehicles may be used alone or in combination.

Auxiliary agents used in the present invention include propellants, surface-active agents, fixing agents, dispersing agents, thickening agents, and bonding agents. Propellants include, for example, liquefied petroleum gas, dimethyl ether, and fluorocarbons. Surface-active agents include, for example, polyoxyethylene alkylaryl ether, polyoxyethylene sorbitane monolaurate, alkylallyl sorbitane monolaurate, alkylbenzene sulfonate, alkylnaphthalene sulfonate, lignin sulfonate, and sulfuric acid ester salts of higher alcohols. These surface-active agents may be used alone or in combination.

Fixing agents, dispersing agents, thickening agents, and bonding agents include, for example, casein, gelatine, starch, carboxymethyl cellulose, alginic acid, agar, polyvinyl alcohol, polyethylene glycol, polysodium acrylate, gum arabic, and xanthane gum, which may be used if required.

The termite control composition for soil treatment of the present invention may contain co-operating agents such as sinepyrin 500, piperonyl butoxide, and S-421.

The termite control composition of the present invention may be used not only for treating the surface or the interior of surrounding soil or under-floor soil for protecting wood such as trees, fences, and railroad ties, or buildings such as houses, warehouses, and industrial plants, but also in timber products such as plywood and furniture, wood products such as particle boards and half boards, and vinyl products such as coated wires and sheets.

The present invention also includes the aspects for preventive uses in places where the breeding of termites is expected as well as the above aspects.

Emulsifying agents which may be used are one or more of those selected from non-ionic or anionic emulsifying agents. Examples of non-ionic emulsifying agents which may be mentioned include polyoxyethylenealkylphenyl ether, polyoxyethylenealkyl ether, polyethyleneglycol fatty ester, sorbitan fatty ester, polyoxyethylene sorbitan fatty ester, polyoxyethylenesorbitol fatty ester, polyoxyethylenepolyoxypropylenealkyl ether. Examples of anionic emulsifying agents which may be mentioned include alkyl sulfates, polyxyethylenealkyl ether, sulfates, sulfosuccinates, taurine derivatives, sarcosine derivatives, phosphoric esters, alkylbenezenesulfonates and the like. A mixture consisting of polyoxyethylenestyrylphenyl ether and calcium alkylbenzenesulfonate is preferred. These emulsifying agents may be used in an amount of 5 to 20 weight parts per 100 weight parts of the composition of the present invention.

Compositions of the present invention may be prepared by any of conventional procedures suitable for emulsifiable concentrates.

The present invention is illustrated by the following examples, comparative examples and experimental examples, but is not limited to the details thereof.

EXAMPLES

Typical embodiments and test examples of the present invention will be shown below, but the present invention is not limited to these embodiments.

In the description of these embodiments, the term "part(s)" means part(s) by weight. The test method of embodiments was in accordance with Japan Wood Preservation Association Standards No. 13, 1987, "Standards for Testing Methods of Termite Controlling Effects and Performance of Termite Controlling Agents for Soil Treatment (I)".

Embodiment 1 Consists of:

| | |
|---|---|
| Compound A | 8.00 parts |
| Bifenthrin | 2.00 parts |
| Propylene glycol | 5.00 parts |
| Anionic surface-active agent | 1.00 part |
| Non-ionic surface-active agent | 5.00 parts |
| Xanthane gum | .25 part |
| Silicone defoaming agent | .50 part |
| Water | 78.25 parts |

The above materials are uniformly mixed and suspended to form a flowable agent.

Embodiment 2 Consists of:

| | |
|---|---|
| Compound A | 1.00 part |
| Bifenthrin | .40 part |
| Propylene glycol | 5.00 parts |
| Anionic surface-active agent | 1.00 part |
| Non-ionic surface-active agent | 5.00 parts |
| Xanthane gum | 0.40 part |
| Silicone defoaming agent | 0.50 part |
| Water | 86.70 parts |

The above materials are uniformly mixed and suspended to form a flowable agent.

Embodiment 3 Consists of:

| | |
|---|---|
| Compound A | 4.00 parts |
| Permethrin | 20.00 parts |
| Anionic surface-active agent | 10.00 parts |
| N-methyl-2-pyrrolidone | 10.00 parts |
| Aromatic solvent | 56.00 parts |

The above materials are uniformly dissolved to form an emulsion.

Test Example 1

A testing apparatus was used in which two glass cylinders (each about 5 cm in diameter and about 12 cm in height) are connected at about 2 cm from the bottom with a glass tube about 1.5 cm in diameter and about 10 cm in length (graduated at 5-mm intervals for 5 cm at the center). The one glass cylinder was filled with about 60 g of non-treated soil adjusted to a moisture content of about 25%, and the other glass cylinder was filled with about 0.29 g of filter paper (5.5 mm in diameter). The glass tube was filled, at a thickness of 1 cm, with test soil prepared by mixing 2.4 g of non-treated sandy soil which had passed through a 20-mesh screen and had been dried at 60° C. until a constant weight had been achieved, with 0.45 g of the solution of the test composition of a predetermined concentration, and the mixture was allowed to stand for 3 weeks in a room without weather resistance treatment. The glass tube was connected to the glass cylinders.

In the glass cylinder filled with non-treated soil, 200 workers and 20 soldiers of *Coptotermes formosanusus* Shiraki were placed, and the testing apparatus was kept at a constant temperature chamber controlled at a temperature of 28° C., and a relative humidity of 70% or higher.

The bored depth (millimeters=mm), damage by eating, and the termite control effect were determined 14 days after insects were put in place, and the effect was evaluated in accordance with the following criteria:

Damage by Eating:

+ 10% or less compared with non-treatment

++ 11–50% or less compared with non-treatment

+++ 51% or more compared with non-treatment

Termite Control Effect:

A 100% lethal

B 80–99% lethal

C 50–79% lethal

D 49% lethal or less

Results are shown in Table 1:

| Embodiments | Test composition | Concentration (%) | Bored depth (mm) 14 DAT | Damage by eating 14 DAT | Termite control effect 14 days later |
|---|---|---|---|---|---|
| | Compound A + bifenthrin | 0.01 + 0.01 | 3 | None | A |
| | | 0.01 + 0.005 | 2 | None | A |
| | | 0.005 + 0.01 | 3 | None | A |
| | | 0.005 + 0.005 | 7 | None | A |
| | | 0.0025 + 0.01 | 5 | None | A |
| | | 0.0025 + 0.005 | 9 | None | A |
| | | 0.00125 + 0.01 | 7 | None | A |
| | | 0.00125 + 0.005 | 9 | None | A |
| | Compound A + fenvalerate | 0.02 + 0.05 | 2 | None | A |
| | | 0.005 + 0.05 | 6 | None | A |
| | | 0.02 + 0.01 | 1 | None | A |
| | | 0.005 + 0.01 | 3 | None | A |
| | Compound A + cypermethrin | 0.02 + 0.025 | 0 | None | A |
| | | 0.005 + 0.025 | 0 | None | A |
| | | 0.02 + 0.005 | 2 | None | A |
| | | 0.005 + 0.005 | 3 | None | A |
| | Compound A + permethrin | 0.02 + 0.1 | 0 | None | A |
| | | 0.005 + 0.1 | 6 | None | A |
| | | 0.02 + 0.02 | 8 | None | A |
| | Compound A + tralomethrin | 0.02 + 0.01 | 6 | None | A |
| | | 0.005 + 0.01 | 4 | None | A |
| | | 0.02 + 0.002 | 2 | None | A |
| | | 0.005 + 0.002 | 8 | None | A |
| | Compound A + fluvalinate | 0.02 + 0.05 | 8 | None | A |
| | Compound A + cyfluthrin | 0.02 + 0.025 | 6 | None | A |
| | | 0.005 + 0.025 | 6 | None | A |
| | | 0.02 + 0.005 | 6 | None | A |
| | Compound A + ethofenprox | 0.02 + 0.1 | 2 | None | A |
| | | 0.005 + 0.1 | 8 | None | A |
| | | 0.02 + 0.02 | 4 | None | A |
| | | 0.005 + 0.02 | 7 | None | A |
| | Compound A + silafluofen | 0.02 + 0.05 | 6 | None | A |
| | | 0.005 + 0.05 | 5 | None | A |
| | | 0.02 + 0.01 | 7 | None | A |

| | Test composition | Concentration (%) | Bored depth (mm) 14 days later | Damage by eating 14 days later | Termite control effect 14 days later |
|---|---|---|---|---|---|
| Comparative | Compound A | 0.02 | >10 | + | A |
| | | 0.01 | >10 | + | A |
| | | 0.005 | >10 | ++ | A |

-continued

| | Test composition | Concentration (%) | Bored depth (mm) 14 days later | Damage by eating 14 days later | Termite control effect 14 days later |
|---|---|---|---|---|---|
| Examples | Bifenthrin | 0.01 | >10 | +++ | D |
| | | 0.005 | >10 | +++ | D |
| | Fenvalerate | 0.05 | >10 | + | A |
| | | 0.01 | >10 | +++ | D |
| | Cypermethrin | 0.025 | >10 | None | D |
| | | 0.005 | >10 | +++ | D |
| | Permethrin | 0.1 | >10 | None | D |
| | | 0.02 | >10 | +++ | D |
| | Tralomethrin | 0.01 | >10 | +++ | D |
| | | 0.002 | >10 | +++ | D |
| | Fluvalinate | 0.05 | >10 | +++ | D |
| | Cyfluthrin | 0.025 | >10 | None | D |
| | | 0.005 | >10 | +++ | D |
| | Ethofenprox | 0.1 | >10 | None | D |
| | | 0.02 | >10 | +++ | D |
| | Silafluofen | 0.05 | >10 | + | A |
| | | 0.01 | >10 | +++ | D |
| | Non-treatment | | >10 | +++ | D |

What is claimed is:

1. A termiticidal combination comprising (a) tralomethrin and (b) 5-amino-3-cyano- 1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10.

2. A combination as claimed in claim 1, wherein the ratio by weight of (a) to (b) is between 0.5 and 5.

3. A termiticidal combination comprising (a) tralomethrin and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.5 and 20.

4. A termiticidal composition comprising:
(a) tralomethrin and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10; and (c) an acceptable carrier therefor.

5. A composition as claimed in claim 4, wherein the ratio by weight of (a) to (b) is between 0.5 and 5.

6. A composition as claimed in claim 4, being in liquid form and comprising from 0.001% to 50% by weight of 5-amino-3-cyano-1-(2,6-dichloro-4-trifluoromethylphenyl)-4-trifluoromethylsulphinylpyrazole.

7. A composition as claimed in claim 5, being in liquid form and comprising from 0.001% to 50% by weight of 5-amino-3-cyano-1-(2,6-dichloro-4-trifluoromethylphenyl)-4-trifluoromethylsulphinylpyrazole.

8. A composition as claimed in claim 6, comprising from 0.005% to 10% by weight of 5-amino-3-cyano-1-(2,6-dichloro-4-trifluoromethylphenyl)-4-trifluoromethylsulphinylpyrazole.

9. A composition as claimed in claim 7, comprising from 0.005% to 10% by weight of 5-amino-3-cyano-1-(2,6-dichloro4-trifluoromethylphenyl)-4-trifluoromethylsulphinylpyrazole.

10. A composition as claimed in claim 4, being in the form of a concentrate and comprising from 1% to 20% by weight of 5-amino-3-cyano-1-(2,6-dichloro4-trifluoromethylphenyl)-4-trifluoromethylsulphinylpyrazole.

11. A composition as claimed in claim 5, being in the form of a concentrate and comprising from 1% to 20% by weight of 5-amino-3-cyano-1-(2,6-dichloro-4-trifluoromethylphenyl)-4-trifluoromethylsulphinylpyrazole.

12. A termiticidal composition comprising:
(a) tralomethrin and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.5 and 20; and (c) an acceptable carrier therefor.

13. A method for controlling termites and for preventing them from passing through a layer of soil or other material, said method comprising treating said layer with a termiticidally effective amount of a termiticidal composition comprising (a) tralomethrin and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10; and (c) an acceptable carrier therefor.

14. A method as claimed in claim 13, wherein the ratio by weight of (a) to (b) is between 0.5 and 5.

15. A method as claimed in claim 13, wherein said composition is in liquid form and comprises from 0.001% to 50% by weight of 5-amino-3-cyano-1-(2,6-dichloro-4-trifluoromethypheny)-4-trifluoromethylsulphininylpyrazole.

16. A method as claimed in claim 14, wherein said composition is in liquid form and comprises from 0.001% to 50% by weight of 5-amino-3-cyano-1-(2,6-dichloro-4-trifluoromethylphenyl)4-trifluoromethylsulphinylpyrazole.

17. A method as claimed in claim 15, wherein said composition comprises from 0.005% to 10% by weight of 5-amino-3-cyano-1-(2,6-dichloro-4-trifluoromethylphenyl)4-trifluoromethylsulphinylpyrazole.

18. A method as claimed in claim 16, wherein said composition comprises from 0.005% to 10% by weight of 5-amino-3-cyano-1-(2,6-dichloro-4-trifluoromethylphenyl)-4-trifluoromethylsulphinylpyrazole.

19. A method as claimed in claim 13, wherein a layer of soil is treated and wherein an amount between 0.01 g/m$^2$ and 7 g/m$^2$ of active ingredients (a) and (b) is applied.

20. A method as claimed in claim 14, wherein a layer of soil is treated and wherein an amount between 0.01 g/m$^2$ and 7 g/m$^2$ of active ingredients (a) and (b) is applied.

21. A method as claimed in claim 19, wherein the amount of active ingredients (a) and (b) applied is between 0.1 g/m$^2$ and 5 glm$^2$.

22. A method as claimed in claim 20, wherein the amount of active ingredients (a) and (b) applied is between 0.1 g/m$^2$ and 5 g/m$^2$.

23. A method for controlling termites and for preventing them from passing through a layer of soil or other material, said method comprising treating said layer with a termiticidally effective amount of a termiticidal composition comprising (a) tralomethrin and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.5 and 20; and (c) an acceptable carrier therefor.

24. A termiticidal combination comprising (a) fluvalinate and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10.

25. A combination as claimed in claim 24, wherein the ratio by weight of (a) to (b) is between 0.5 and 5.

26. A termiticidal composition comprising:
(a) fluvalinate and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10; and (c) an acceptable carrier therefor.

27. A composition as claimed in claim 26, wherein the ratio by weight of (a) to (b) is between 0.5 and 5.

28. A composition as claimed in claim 26, being in liquid form and comprising from 0.001% to 50% by weight of 5-amino-3-cyano-1-(2,6-dichloro-4-trifluoromethylphenyl)-4-trifluoromethylsulphinylpyrazole.

29. A composition as claimed in claim 27, being in liquid form and comprising from 0.001% to 50% by weight of 5-amino-3-cyano-1-(2,6-dichloro-4trifluoromethylphenyl)-4-trifluoromethylsulphinylpyrazole.

30. A composition as claimed in claim 28, comprising from 0.005% to 10% by weight of 5-amino-3-cyano-1-(2,6-dichloro-4-trifluoromethylphenyl)-4-trifluoromethylsulphinylpyrazole.

31. A composition as claimed in claim 29, comprising from 0.005% to 10% by weight of 5-amino-3-cyano-1-(2,6-dichloro-4-trifluoromethylphenyl)-4-trifluoromethylsulphinylpyrazole.

32. A composition as claimed in claim 26, being in the form of a concentrate and comprising from 1% to 20% by weight of 5-amino-3-cyano-1-(2,6-dichloro-4-trifluoromethylphenyl)4-trifluoromethylsulphinylpyrazole.

33. A composition as claimed in claim 27, being in the form of a concentrate and comprising from 1% to 20% by weight of 5-amino-3-cyano-1-(2,6-dichloro-4-trifluoromethylphenyl)-4-trifluoromethylsulphinylpyrazole.

34. A method for controlling termites and for preventing them from passing through a layer of soil or other material, said method comprising treating said layer with a termiticidally effective amount of a termiticidal composition comprising (a) fluvalinate and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10; and (c) an acceptable carrier therefor.

35. A method as claimed in claim 34, wherein the ratio by weight of (a) to (b) is between 0.5 and 5.

36. A method as claimed in claim 34, wherein said composition is in liquid form and comprises from 0.001% to 50% by weight of 5-amino-3-cyano-1-(2,6-dichloro-4-trifluoromethylphenyl)-4-trifluoromethylsulphinylpyrazole.

37. A method as claimed in claim 35, wherein said composition is in liquid form and comprises from 0.001% to 50% by weight of 5-amino-3-cyano-1-(2,6-dichloro-4-trifluoromethylphenyl)-4-trifluoromethylsulphinylpyrazole.

38. A method as claimed in claim 36, wherein said composition comprises from 0.005% to 10% by weight of 5-amino-3-cyano-1-(2,6-dichloro-4-trifluoromethylphenyl)-4-trifuoromethylsulphinylpyrazole.

39. A method as claimed in claim 37, wherein said composition comprises from 0.005% to 10% by weight of 5-amino-3-cyano-1-(2,6-dichloro-4-trifluoromethylphenyl)-4-trifluoromethylsulphinylpyrazole.

40. A method as claimed in claim 34, wherein a layer of soil is treated and wherein an amount between 0.01 g/m$^2$ and 7 g/m$^2$ of active ingredients (a) and (b) is applied.

41. A method as claimed in claim 35, wherein a layer of soil is treated and wherein an amount between 0.01 g/m$^2$ and 7 g/m$^2$ of active ingredients (a) and (b) is applied.

42. A method as claimed in claim 40, wherein the amount of active ingredients (a) and (b) applied is between 0.1 g/m$^2$ and 5 g/m$^2$.

43. A method as claimed in claim 41, wherein the amount of active ingredients (a) and (b) applied is between 0.1 g/m$^2$ and 5 g/m$^2$.

44. A termiticidal combination comprising (a) cyfluthrin and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10.

45. A combination as claimed in claim 44, wherein the ratio by weight of (a) to (b) is between 0.5 and 5.

46. A termiticidal composition comprising:
(a) cyfluthrin and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10; and (c) an acceptable carrier therefor.

47. A composition as claimed in claim 46, wherein the ratio by weight of (a) to (b) is between 0.5 and 5.

48. A composition as claimed in claim 46, being in liquid form and comprising from 0.001% to 50% by weight of 5-amino-3-cyano-1-(2,6-dichloro-4-trifluoromethylphenyl)-4-trifluoromethylsulphinylpyrazole.

49. A composition as claimed in claim 47, being in liquid form and comprising from 0.001% to 50% by weight of 5-amino-3-cyano-1-(2,6-dichloro-4-trifluoromethylphenyl)-4-trifluoromethylsulphinylpyrazole.

50. A composition as claimed in claim 48, comprising from 0.005% to 10% by weight of 5-amino-3-cyano-1-(2,6-dichloro-4-trifluoromethylphenyl)-4-trifluoromethylsulphinylpyrazole.

51. A composition as claimed in claim 49, comprising from 0.005% to 10% by weight of 5-amino-3-cyano-1-(2,6-dichloro-4-trifluoromethylphenyl)-4-trifluoromethylsulphinylpyrazole.

52. A composition as claimed in claim 46, being in the form of a concentrate and comprising from 1% to 20% by weight of 5-amino-3-cyano-1-(2,6-dichloro-4-trifluoromethylphenyl)4-trifluoromethylsulphinylpyrazole.

53. A composition as claimed in claim 47, being in the form of a concentrate and comprising from 1% to 20% by weight of 5-amino-3-cyano-1-(2,6-dichloro4-trifluoromethylphenyl)-4-trifluoromethylsulphinylpyrazole.

54. A method for controlling termites and for preventing them from passing through a layer of soil or other material, said method comprising treating said layer with a termiticidally effective amount of a termiticidal composition comprising (a) cyfluthrin and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10; and (c) an acceptable carrier therefor.

55. A method as claimed in claim 54, wherein the ratio by weight of (a) to (b) is between 0.5 and 5.

56. A method as claimed in claim 54, wherein said composition is in liquid form and comprises from 0.001% to 50% by weight of 5-amino-3-cyano-1-(2,6-dichloro-4-trifluoromethylphenyl)-4-trifluoromethylsulphinylpyrazole.

57. A method as claimed in claim 55, wherein said composition is in liquid form and comprises from 0.001% to 50% by weight of 5-amino-3-cyano-1-(2,6-dichloro-4-trifluoromethylphenyl)-4-trifluoromethylsulphinylpyrazole.

58. A method as claimed in claim 56, wherein said composition comprises from 0.005% to 10% by weight of 5-amino-3-cyano-1-(2,6-dichloro-4-trifluoromethylphenyl) 4-trifluoromethylsulphinylpyrazole.

59. A method as claimed in claim 57, wherein said composition comprises from 0.005% to 10% by weight of 5-amino-3-cyano-1-(2,6-dichloro-4-trifluoromethylphenyl)-4-trifluoromethylsulphinylpyrazole.

60. A method as claimed in claim 54, wherein a layer of soil is treated and wherein an amount between 0.01 g/m$^2$ and 7 g/m$^2$ of active ingredients (a) and (b) is applied.

61. A method as claimed in claim 55, wherein a layer of soil is treated and wherein an amount between 0.01 g/m$^2$ and 7 g/m$^2$ of active ingredients (a) and (b) is applied.

62. A method as claimed in claim 60, wherein the amount of active ingredients (a) and (b) applied is between 0.1 g/m$^2$ and 5 g/m$^2$.

63. A method as claimed in claim 61, wherein the amount of active ingredients (a) and (b) applied is between 0.1 g/m$^2$ and 5 g/m$^2$.

64. A termiticidal combination comprising (a) silafluofen and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10.

65. A combination as claimed in claim 64, wherein the ratio by weight of (a) to (b) is between 0.5 and 5.

66. A termiticidal composition comprising:
(a) silafluofen and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10; and (c) an acceptable carrier therefor.

67. A composition as claimed in claim 66, wherein the ratio by weight of (a) to (b) is between 0.5 and 5.

68. A composition as claimed in claim 66, being in liquid form and comprising from 0.001% to 50% by weight of 5-amino-3-cyano-1-(2,6-dichloro-4-trifluoromethylphenyl) 4-trifluoromethylsulphinylpyrazole.

69. A composition as claimed in claim 67, being in liquid form and comprising from 0.001% to 50% by weight of 5-amino-3-cyano-1-(2,6-dichloro-4-trifluoromethylphenyl)-4-trifluoromethylsulphinylpyrazole.

70. A composition as claimed in claim 68, comprising from 0.005% to 10% by weight of 5-amino-3-cyano-1-(2,6-dichloro-4-trifluoromethylphenyl)-4-trifluoromethylsulphinylpyrazole.

71. A composition as claimed in claim 69, comprising from 0.005% to 10% by weight of 5-amino-3-cyano-1-(2,6-dichloro-4-trifluoromethylphenyl)-4-trifluoromethylsulphinylpyrazole.

72. A composition as claimed in claim 66, being in the form of a concentrate and comprising from 1% to 20% by weight of 5-amino-3-cyano-1-(2,6-dichloro-4-trifluoromethylphenyl)-4-tifluoromethylsulphinylpyrazole.

73. A composition as claimed in claim 67, being in the form of a concentrate and comprising from 1% to 20% by weight of 5-amino-3-cyano-1-(2,6-dichloro-4-trifluoromethylphenyl)-4-trifluoromethylsulphinylpyrazole.

74. A method for controlling termites and for preventing them from passing through a layer of soil or other material, said method comprising treating said layer with a termiticidally effective amount of a termiticidal composition comprising (a) silafluofen and (b) 5-amino-3-cyano-1-(2,6-dichloro-4-trifluoromethylphenyl)-4-trifluoromethylsulphinylpyrazole, in a combined synergistic termiticidally effective amount, the ratio by weight of (a) to (b) being between 0.1 and 10; and (c) an acceptable carrier therefor.

75. A method as claimed in claim 74, wherein the ratio by weight of (a) to (b) is between 0.5 and 5.

76. A method as claimed in claim 74, wherein said composition is in liquid form and comprises from 0.001% to 50% by weight of 5-amino-3-cyano-1-(2,6-dichloro-4-trifluoromethylphenyl)-4-trifluoromethylsulphinylpyrazole.

77. A method as claimed in claim 75, wherein said composition is in liquid form and comprises from 0.001% to 50% by weight of 5-amino-3-cyano-1-(2,6-dichloro-4-trifluoromethylphenyl)-4-trifluoromethylsulphinylpyrazole.

78. A method as claimed in claim 76, wherein said composition comprises from 0.005% to 10% by weight of 5-amino-3-cyano-1-(2,6-dichloro-4-trifluoromethylphenyl)-4-trifluoromethylsulphinylpyrazole.

79. A method as claimed in claim 77, wherein said composition comprises from 0.005 to by weight of 5-amino-3-cyano-1-(2,6-dichloro-4-trifluoromethylphenyl)-4-trifluoromethylsulphinylpyrazole.

80. A method as claimed in claim 74, wherein a layer of soil is treated and wherein an amount between 0.01 g/m$^2$ and 7 g/m$^2$ of active ingredients (a) and (b) is applied.

81. A method as claimed in claim 75, wherein a layer of soil is treated and wherein an amount between 0.01 g/m$^2$ and 7 g/m$^2$ of active ingredients (a) and (b) is applied.

82. A method as claimed in claim 80, wherein the amount of active ingredients (a) and (b) applied is between 0.1 g/m$^2$ and 5 g/m$^2$.

83. A method as claimed in claim 81, wherein the amount of active ingredients (a) and (b) applied is between 0.1 g/m$^2$ and 5 g/m$^2$.

* * * * *